United States Patent
Deepak et al.

(10) Patent No.: US 10,034,610 B2
(45) Date of Patent: Jul. 31, 2018

(54) SYSTEM AND METHOD FOR REGISTRATION OF BRAIN IMAGES

(71) Applicant: Infosys Limited, Bangalore (IN)

(72) Inventors: Krishnamurty Sai Deepak, Bangalore (IN); Radha Krishna Pisipati, Hyderabad (IN); Harikrishna Gandhinagara Narayana Rai, Bangalore (IN)

(73) Assignee: Infosys Limited, Bangalore (IN)

( * ) Notice: Subject to any disclaimer, the term of this patent is extended or adjusted under 35 U.S.C. 154(b) by 215 days.

(21) Appl. No.: 14/973,428

(22) Filed: Dec. 17, 2015

(65) Prior Publication Data

US 2016/0189382 A1    Jun. 30, 2016

(30) Foreign Application Priority Data

Dec. 24, 2014   (IN) ............ 6535/CHE/2014

(51) Int. Cl.
| | | |
|---|---|---|
| *G06K 9/00* | (2006.01) | |
| *A61B 5/00* | (2006.01) | |
| *A61B 5/055* | (2006.01) | |
| *G06T 7/33* | (2017.01) | |

(52) U.S. Cl.
CPC ............ *A61B 5/0042* (2013.01); *A61B 5/055* (2013.01); *G06T 7/33* (2017.01); *G06T 2207/10081* (2013.01); *G06T 2207/10088* (2013.01); *G06T 2207/20016* (2013.01); *G06T 2207/30016* (2013.01)

(58) Field of Classification Search
None
See application file for complete search history.

(56) References Cited

U.S. PATENT DOCUMENTS

| | | | |
|---|---|---|---|
| 7,263,243 B2 | 8/2007 | Chen et al. | |
| 7,561,757 B2* | 7/2009 | Sabuncu | G06K 9/6206 382/128 |
| 7,995,864 B2 | 8/2011 | Mullick et al. | |
| 8,369,931 B2 | 2/2013 | Paek et al. | |
| 8,442,285 B2 | 5/2013 | Madabhushi et al. | |
| 8,611,692 B2* | 12/2013 | Nimnual | G06T 3/0068 382/276 |
| 9,483,816 B2* | 11/2016 | Smith | G06T 7/00 |

(Continued)

OTHER PUBLICATIONS

Wang, C. Y., Lee, T. F., & Fang, C. H. (2009). 3D volumetric visualization with automatic rigid and deformable hybrid image registration for adaptive radiotherapy. J Cancer Sci Ther, 1, 041-046.*

(Continued)

*Primary Examiner* — Vu Le
*Assistant Examiner* — Samah Beg
(74) *Attorney, Agent, or Firm* — Klarquist Sparkman, LLP

(57) ABSTRACT

A method and a system for registering multi-modal brain images includes registering two or more full volumes of brain images based on a projection based reference image. The registration is based on sharing of mass in a predetermined direction such as axial, sagittal and coronal direction. After the registration of two or more brain images, a two or more partial volumes in a region of interest is registered through a modified mutual information. The modified mutual information may be a factor of an overlap rate and a weight assigned to it.

20 Claims, 5 Drawing Sheets

(56) References Cited

U.S. PATENT DOCUMENTS

| | | | |
|---|---|---|---|
| 9,740,950 B1* | 8/2017 | Jin | G06K 9/3233 |
| 2003/0216631 A1* | 11/2003 | Bloch | G06T 3/0081 |
| | | | 600/407 |
| 2004/0234113 A1* | 11/2004 | Miga | G06T 7/0012 |
| | | | 382/128 |
| 2005/0078881 A1* | 4/2005 | Xu | G06K 9/6211 |
| | | | 382/294 |
| 2005/0271302 A1* | 12/2005 | Khamene | G06K 9/00986 |
| | | | 382/294 |
| 2006/0029291 A1* | 2/2006 | Sun | G06K 9/6212 |
| | | | 382/294 |
| 2006/0165267 A1* | 7/2006 | Wyman | G06T 7/32 |
| | | | 382/128 |
| 2007/0167784 A1* | 7/2007 | Shekhar | A61B 6/032 |
| | | | 600/443 |
| 2009/0046951 A1* | 2/2009 | Paragios | G06K 9/32 |
| | | | 382/294 |
| 2010/0111420 A1* | 5/2010 | Mattes | G06T 7/33 |
| | | | 382/190 |
| 2010/0324410 A1 | 12/2010 | Paek et al. | |
| 2010/0329529 A1* | 12/2010 | Feldman | G06K 9/6252 |
| | | | 382/131 |
| 2011/0085716 A1* | 4/2011 | Chefd'hotel | G06K 9/6215 |
| | | | 382/128 |
| 2012/0038649 A1* | 2/2012 | Kanitsar | G06T 11/003 |
| | | | 345/440 |
| 2013/0004085 A1* | 1/2013 | Bai | G06T 3/0068 |
| | | | 382/209 |
| 2014/0003696 A1* | 1/2014 | Taghva | A61B 5/0037 |
| | | | 382/131 |
| 2014/0037172 A1* | 2/2014 | Madabhushi | G06K 9/6232 |
| | | | 382/131 |
| 2014/0334709 A1* | 11/2014 | Siewerdsen | G06T 7/0026 |
| | | | 382/132 |
| 2015/0030221 A1* | 1/2015 | Lou | G06T 3/0068 |
| | | | 382/131 |
| 2015/0085981 A1* | 3/2015 | Siewerdsen | A61B 19/00 |
| | | | 378/63 |
| 2015/0317788 A1* | 11/2015 | van Baar | G06T 7/0012 |
| | | | 382/128 |
| 2016/0133037 A1* | 5/2016 | Vemulapalli | G06T 11/60 |
| | | | 382/128 |
| 2016/0242745 A1* | 8/2016 | Yang | A61B 8/5261 |
| 2016/0302747 A1* | 10/2016 | Averbuch | G06T 19/006 |
| 2017/0228896 A1* | 8/2017 | Yu | G06T 7/149 |

OTHER PUBLICATIONS

Studholme, C., Hill, D. L., & Hawkes, D. J. (1999). An overlap invariant entropy measure of 3D medical image alignment. Pattern recognition, 32(1), 71-86.*

Alexandre Guimond, Alexis Roche, Nicholas Ayache, Jean Meunier. Multimodal Brain Warping Using the Demons Algorithm and Adaptative Intensity Corrections. IEEE Transaction on Medical Imaging, undened or unknown publisher, 2001, 20 (1), pp. 58-69.*

Wells, W. M., Viola, P., Atsumi, H., Nakajima, S., & Kikinis, R. (1996). Multi-modal volume registration by maximization of mutual information. Medical image analysis, 1(1), 35-51.*

Jenkinson et al., "Improved Optimization for the Robust and Accurate Linear Registration and Motion Correction of Brain Images," *NeuroImage*, vol. 17, 2002, pp. 825-841, 17 pages.

Pluim et al., "Image Registration by Maximization of Combined Mutual Information and Gradient Information," *Medical Image Computing and Computer-Assisted Intervention—MICCAI 2000*, vol. 1935 of the series Lecture Notes in Computer Science, 2000, pp. 452-461, 6 pages.

Kapur, "Segmentation of brain tissue from magnetic resonance images," Thesis paper, Massachusetts Institute of Technology, Feb. 1995, 86 pages.

* cited by examiner

SYSTEM AND METHOD FOR REGISTRATION OF BRAIN IMAGES

FIELD OF TECHNOLOGY

The field relates to a method, system and/or apparatus for registration of brain images and in particular to a method, system and/or apparatus for registration of brain images based on modified mutual information.

BACKGROUND

Surgical procedures such as resective surgery and Deep Brain stimulation (DBS) on deep brain structures require effective post-operative procedures for analysis of surgical success. The surgical procedures also enable medical experts to plan therapy and further surgical procedures, if any. Magnetic Resonance Imaging (MRI) and Computed Tomography (CT) are integral to the surgical procedures. MRI and CT images may be acquired before and after the surgical procedures to determine a level of success of the surgical procedures. In the case of resective surgery for epilepsy as well as DBS, a goal is to localize a set of electrodes placed within brain during surgery using images acquired from MRI and CT images. An MRI image may provide organ-level detail in the brain whereas a CT image may provide high contrast for electrodes. Spatially aligning the MRI and CT images is known as registration. Further, fusing the MRI and CT images helps medical experts in localizing the electrodes.

SUMMARY

Disclosed are a method, an apparatus and/or a system of registration of brain images.

In one aspect, a computer-implemented method for registration of brain images is disclosed. The method includes registering two or more full volumes of the brain images based on a projection based reference image. The registration is performed based on sharing of mass in a predetermined direction. Two or more partial volumes in the region of interest is registered through a modified mutual information. The modified mutual information is a factor of an overlap rate and a weight assigned to the overlap rate. The modified mutual information is based on the normalization of a mutual information. The mutual information may be normalized to get an average value obtained from the mutual information. A transformation function may be defined to map one or more registration points with another registration point. The sharing of mass may be performed by calculating rotation of the two or more full volumes of brain images in an axial, a sagittal and a coronal direction. The sharing of mass may further comprise steps to calculate translation of the two or more full volumes of brain images in an axial, a sagittal and a coronal direction. One or more convergence criterion are applied to complete the registration of the two or more two full volumes of brain images. The two or more full volumes of brain images may be an image obtained through a computed tomography technique and/or a magnetic resonance imaging technique.

In another aspect, a system for a multi-modal image registration is disclosed. The system includes a coarse registration module and a fine registration module. The fine registration module is communicatively coupled with coarse registration module. The coarse registration module registers the two or more multi-modal brain images through a projection based reference image. The coarse registration module further identifies regions of clinical interest. The fine registration module registers the two or more multi-modal brain images on the identified regions of clinical interest using a modified mutual information. The course registration module may perform course registration based on sharing of mass in a predetermined directions. The modified mutual information is based on normalization of mutual information. The mutual information may be normalized to get an average value obtained from the mutual information. The modified mutual information is a factor of an overlap rate and a weight assigned to the overlap rate. The sharing of mass may be performed by calculating rotation of the one or more multi-modal brain images in an axial, a sagittal and a coronal direction. The sharing of mass may further comprise steps to calculate translation of the two or more multi-modal brain images in an axial, a sagittal and a coronal direction. One or more convergence criterion are applied to complete the coarse registration of the two or more multi-modal brain images. The two or more multi-modal brain images may be an image obtained through a computed tomography technique and/or a magnetic resonance imaging technique.

In another aspect, a computer-implemented method of registration of multi-modal brain images is disclosed. The method includes receiving two or more multi-modal brain images. One or more registration points are identified in the two or more multi-modal brain images. A transformation function through a modified mutual information is defined. The transformation function is applied to map the one or more registration points with another registration point. The two or more multi-modal brain images are registered through interpolation. The interpolation may be performed based on linear interpolation technique. The two or more multi-modal brain images are processed by applying one or more filters. The modified mutual information is based on normalization of mutual information. The mutual information may be normalized to get an average value obtained from the mutual information. The modified mutual information is a factor of an overlap rate and a weight assigned to the overlap rate. The two or more multi-modal brain image may be an image obtained through a computed tomography technique and/or a magnetic resonance imaging technique.

In an additional aspect, a computer-implemented method for fusing two or more brain images based on a modified mutual information is disclosed. The method includes detecting one or more registration points in the two or more brain images. The one or more registration points are registered based on a modified mutual information. A fused image of the two or more brain images are generated. A transformation function may be defined to map the one or more registration point with another registration point. The registration point may contain one or more deep brain structures. The modified mutual information may be based on normalization of mutual information. The mutual information may be normalized to get an average value obtained from the mutual information. The modified mutual information is a factor of an overlap rate and a weight assigned to the overlap rate. The two or more brain images may be an image obtained through a computed tomography technique and/or a magnetic resonance imaging technique.

The methods and systems disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

The embodiments of this invention are illustrated by way of example and not limitation in the figures of the accompanying drawings, in which like references indicate similar elements and in which.

Figure 1:
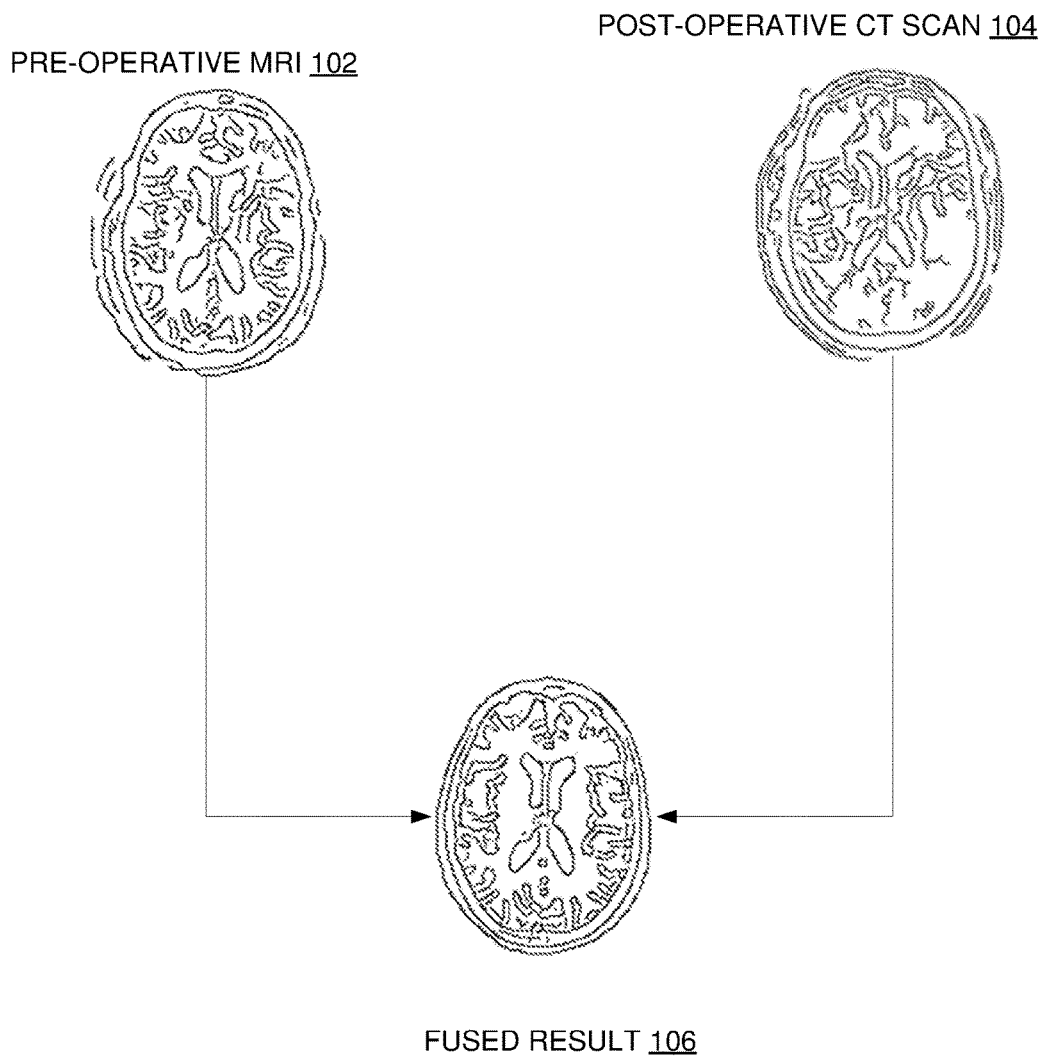
FIG. 1 is diagrammatic representation of fusing brain images to obtain a fused result, according to one or more embodiments.

Other features of the present embodiments will be apparent from the accompanying drawings and from the detailed description that follows.

DETAILED DESCRIPTION

Example embodiments, as described below, may be used to provide a method, an apparatus and/or a system of registration of brain images. Although the present embodiments have been described with reference to specific example embodiments, it will be evident that various modifications and changes may be made to these embodiments without departing from the broader spirit and scope of the various embodiments.

Image registration in deep brain surgery may be necessary as image registration helps in localization of electrode placement with respect to surrounding brain structures and better visualization. 3-Dimensional (3D) visualization may help define more accurate stimulation parameters and may highly improve patient experience by avoiding multiple sessions to refine stimulation parameters.

In an example embodiment, a coarse to fine approach for rigid registration may involve 3 rotations and 3 translations. During coarse registration, a computed tomography (CT) scan image and magnetic resonance imaging (MRI) image may be roughly aligned. During fine registration, the alignment between the CT image and the MRI image may be refined based on a similarity measure.

In one or more embodiments, a method of image registration may include one or more of the following steps: pre-processing, mutual information, rigid transformation and interpolation.

In one or more embodiments, pre-processing may be necessary in order to improve input and reference image quality. Image enhancements may be performed by applying filters to remove any possible noise. Low-pass filtering and/or median filters may be applied to remove speckle noise in images. Images may also be normalized. Window-levelling may be performed as images from different modalities are getting registered. Both input and reference images may be resized to have equal width and height. In one or more embodiments, Shannon entropy may provide an absolute limit on a possible average length of lossless encoding and/or compression of communication. Shannon entropy measure may be used for computing a mutual information measure. The size of the overlapping part of the images may influence the mutual information measure in different ways. Hence, a normalized measure of mutual information (NMI) which is less sensitive to changes in overlap may be adopted. NMI may be used to identify registration points in sample and/or reference image.

Post identification of the registration points, next step may be to define a transformation function to map the registration points. Transformation applied to register the images may be categorized according to the degrees of freedom. Rigid transformation may include only translations and may be sufficient to register images of rigid objects. Other transformation techniques such as affine transformation may allow scaling and shearing.

Further, when transforming points from one image to another, interpolation may be required to estimate a grey value of the resulting point in a registration process. In addition, interpolation may be required to yield the registered image. Since interpolation may be performed only once, speed is less of an issue and a different choice of interpolation method may be more appropriate. In an example embodiment, linear interpolation may be the interpolation method adopted. Liner interpolation method may define an intensity of a point as the weighted combination of intensities of the point's neighbors. The weights may be linearly dependent on the distance between the point and the point's neighbors.

FIG. 1 is diagrammatic representation of fusing brain images to obtain a fused result, according to one embodiment. A pre-operative MRI scan 102 may shows details of deep brain structures and slow acquisition. A post-operative CT scan 104 may be very sensitive to density such as presence of metallic structures and may further display a fast acquisition process. A pre-operative MRI scan 102 and a post-operative CT scan 104 may be fused to obtain a fused result 106.

Deep rain stimulation (DBS) surgery may be a microelectrode-guided surgery for treatment of patients with movement disorders. The patients may not be treated by medication. Effectiveness of DBS surgery may mainly depend on proper implantation DBS electrode arrays into a selected target areas in brain. Brain shift analysis may be a very important stage of the DBS surgery where a pre-operative MRI scan 102 and the post-operative CT scan 104 may be compared to measure a brain shift. Image registration techniques may be used for analyzing the brain shift during the DBS surgery using the pre-operative MRI scan 102 and the post-operative CT scan 104. Rigid registration techniques may be used in a variety clinical applications such as image-guided therapy, surgical planning and navigation, intraoperative brain deformation analysis and analysis of brain changes associated with tumor growth, multiple sclerosis, Alzheimer's disease and schizophrenia.

Image registration may include the following steps:
(a) Feature detection: Salient and distinctive objects (Example: closed-boundary regions, edges, contours, line intersections, and corners.) in both reference and sensed images may be detected.
(b) Feature matching: The correspondence between the features in the reference and sensed image established.
(c) Transform model estimation: The type and parameters of mapping functions, aligning the sensed image with the reference image, may be estimated.

(d) Image resampling and transformation: The sensed image may be transformed by means of the mapping functions.

Figure 2:
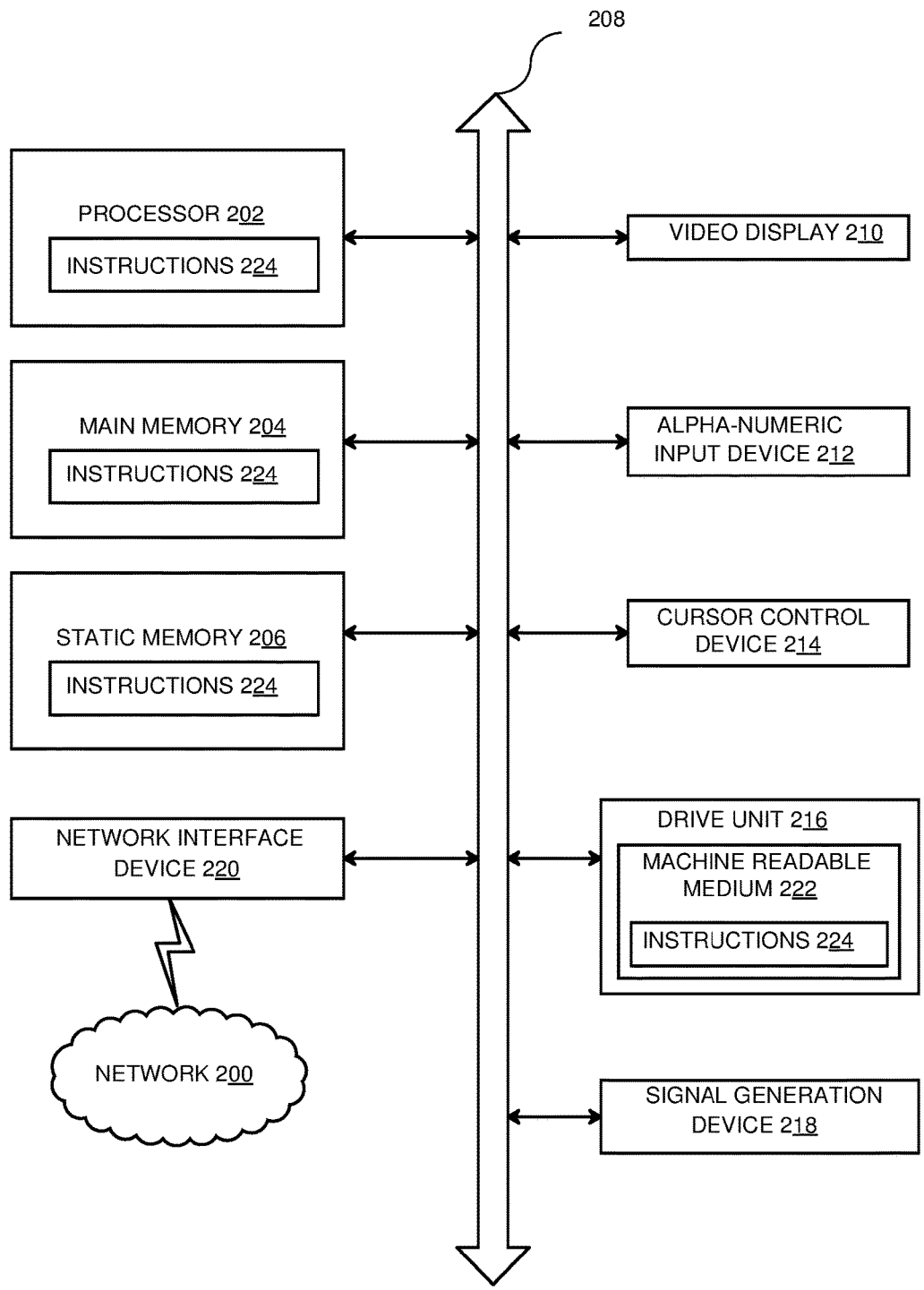
FIG. 2 is a diagrammatic representation of a data processing system capable of processing a set of instructions to perform any one or more of the methodologies herein, according to one embodiment.

FIG. 2 is a diagrammatic representation of a data processing system capable of processing a set of instructions to perform any one or more of the methodologies herein, according to an example embodiment. FIG. 2 shows a diagrammatic representation of machine in the example form of a computer system 200 within which a set of instructions, for causing the machine to perform any one or more of the methodologies discussed herein, may be executed. In various embodiments, the machine operates as a standalone device and/or may be connected (e.g., networked) to other machines.

In a networked deployment, the machine may operate in the capacity of a server and/or a client machine in server-client network environment, and or as a peer machine in a peer-to-peer (or distributed) network environment. The machine may be a personal-computer (PC), a tablet PC, a set-top box (STB), a Personal Digital Assistant (PDA), a cellular telephone, a web appliance, a network router, switch and or bridge, an embedded system and/or any machine capable of executing a set of instructions (sequential and/or otherwise) that specify actions to be taken by that machine. Further, while only a single machine is illustrated, the term "machine" shall also be taken to include any collection of machines that individually and/or jointly execute a set (or multiple sets) of instructions to perform any one and/or more of the methodologies discussed herein.

The example computer system 200 includes a processor 202 (e.g., a central processing unit (CPU) a graphics processing unit (GPU) and/or both), a main memory 204 and a static memory 206, which communicate with each other via a bus 208. The computer system 200 may further include a video display unit 210 (e.g., a liquid crystal displays (LCD) and/or a cathode ray tube (CRT)). The computer system 200 also includes an alphanumeric input device 212 (e.g., a keyboard), a cursor control device 214 (e.g., a mouse), a disk drive unit 216, a signal generation device 218 (e.g., a speaker) and a network interface device 220.

The disk drive unit 216 includes a machine-readable medium 222 on which is stored one or more sets of instructions 224 (e.g., software) embodying any one or more of the methodologies and/or functions described herein. The instructions 224 may also reside, completely and/or at least partially, within the main memory 204 and/or within the processor 202 during execution thereof by the computer system 200, the main memory 204 and the processor 202 also constituting machine-readable media.

The instructions 224 may further be transmitted and/or received over a network 226 via the network interface device 220. While the machine-readable medium 222 is shown in an example embodiment to be a single medium, the term "machine-readable medium" should be taken to include a single medium and/or multiple media (e.g., a centralized and/or distributed database, and/or associated caches and servers) that store the one or more sets of instructions. The term "machine-readable medium" shall also be taken to include any medium that is capable of storing, encoding and/or carrying a set of instructions for execution by the machine and that cause the machine to perform any one or more of the methodologies of the various embodiments. The term "machine-readable medium" shall accordingly be taken to include, but not be limited to, solid-state memories, optical, and magnetic media.

Figure 3:
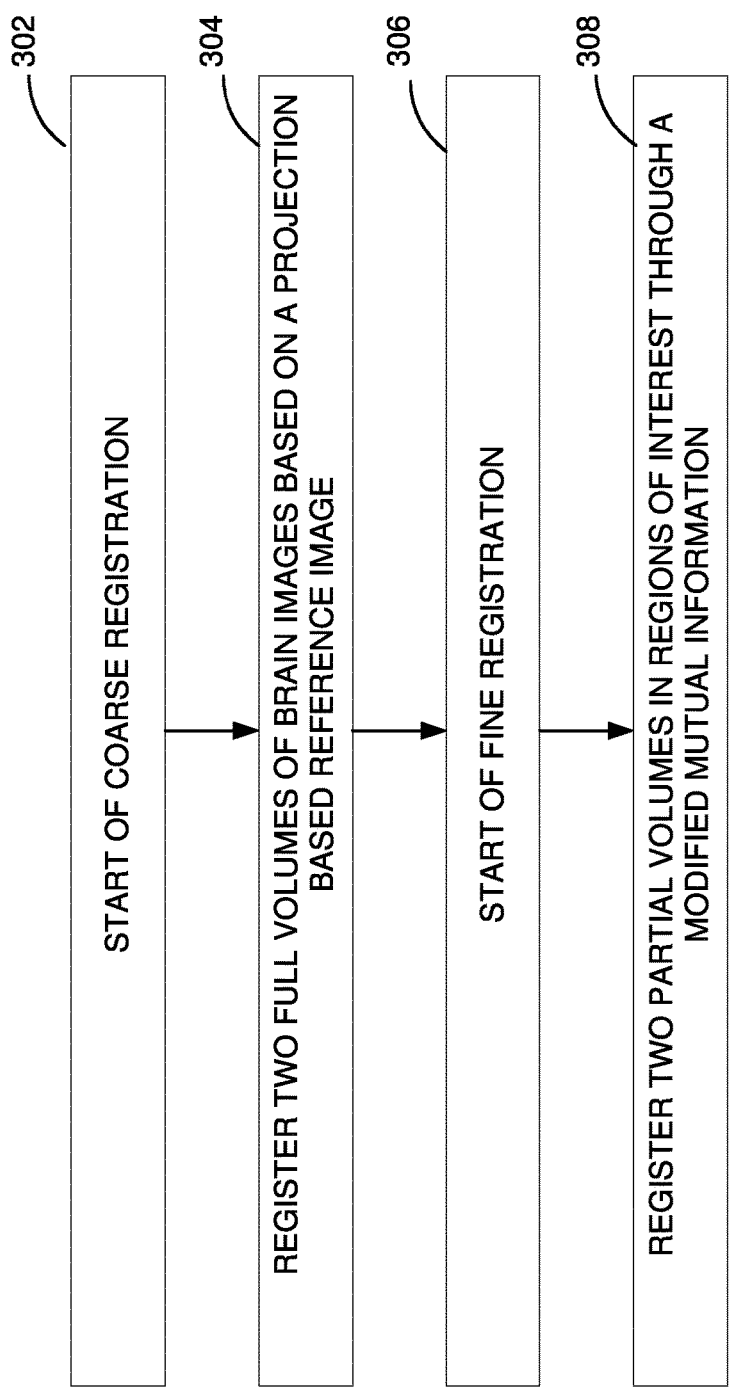
FIG. 3 is a process flow diagram detailing the operations of a method of registration of brain mages, according to one or more embodiments.

FIG. 3 is a process flow diagram detailing the operations of a method of registration of brain mages, according to one or more embodiments. In one or more embodiments, a method of registration of brain images may include coarse registration 302, registering two full volumes of brain images based on a projection based reference image 304, followed by a start of fine registration 306 and registering two partial volumes in regions of interest through modified mutual information 308.

FIG. 3 is a process flow diagram detailing the operations of a method of registration of brain images, according to one or more embodiments. The method includes coarse registration, as in step 302. Two or more full volumes of brain images may be registered based on a projection based reference image, as in step 304. The registration may be performed based on sharing of mass in a predetermined directions.

The course registration (302 and 304) of the two or more full volumes of brain images may be performed based on sharing of mass in a predetermined directions. A brain atlas may be used to determine the distribution of mass in the predetermined directions. The predetermined directions may be an axial, a sagittal and/or a coronal direction. A voxel in the brain atlas may contribute to distribution of mass in the predetermined directions. Steps performed in the coarse registration may be to perform a rotation and/or a translation of the two or more full volumes of brain images. Therefore, the two or more full volumes of brain images may have similar mass distributions in the predetermined directions similar to the brain atlas.

The brain atlas and the two or more full volumes of the brain images are of large size. Therefore one or more projections may be considered in the predetermined directions to perform the rotation and the translation of the two or more full volumes of brain images. The projections may reduce size and computational complexity. A convergence criteria may be applied to complete the coarse registration. The convergence criteria may be defined based on threshold on a residual errors of individual orientations in the predetermined directions. The convergence criteria may also be determined based on an average of the residual errors in the predetermined directions.

After the coarse registration is complete, a fine registration may be initiated, as in step 306. Two or more partial volumes in one or more regions of interest may be registered through a modified mutual information, as in step 308.

Consider an image in the two or more full volumes of brain images to be one of a CT image and/or a MRI image. For the CT image, the one or more regions of interest may be identified using Hounsfield units. Since fat has a Hounsfield unit of −50 (fifty), voxels with greater value may be considered as a possible area within the one or more regions of interest. The above step may remove background in the CT image other than a head rest. The head rest may be removed by computing an eccentricity of connected components and removing the components with the eccentricity greater than a predefined value.

For the MRI image, a background may be determined based on gray level morphological operations. The determined background may be subtracted and an adaptive threshold is applied to generate a binary region of interest. One or more of, but not limited to noisy pixels and/or holes, may be corrected using the morphological operations. Size of morphological operators may be determined from a Digital Imaging and Communications in Medicine (DICOM) headers of the CT image and the MRI image.

The registration of two or more partial volumes in the one or more regions of interest may be termed as fine registration. An image in the two or more partial volume may be one of a CT volume and/or MRI volume. The fine registration may work on a result of the coarse registration. In the fine registration critical regions may be considered for registration. The critical regions may be a region in brain, where a surgical procedures are performed. In the fine registration, one or more volumetric regions of may be selected from the one or more partial volumes of brain mages. The one or more volumetric regions may be registered with each other to derive a final transformation values required for the fine registration.

Consider a case that top view of a head is always present in the CT image and the MRI image. Since skull is visible in the CT image, a first axial slice containing the top view of the head may be selected. One or more successive slices of predetermined dimension (thickness) may be selected. A scale for the dimension may be in millimeter (mm). Similarly, thickness of the one or more regions of interest may be selected in a sagittal and coronal directions based on the predetermined dimension. The fine registration may be performed on the one or more regions of interest of the one or more partial volumes based on a modified mutual information.

In probability theory and information theory, a mutual information (MI) of two random variables is a measure of the variables' mutual dependence. The mutual information is not limited to a real-valued random variables like a correlation coefficient. MI is more general and determines how similar the joint distribution is, to the products of factored marginal distribution. The most common unit of measurement of the mutual information is a bit.

The mutual information may be proposed as a registration measure literature study for multimodality images. The mutual information may be based on an assumption that regions of similar tissue with grey values in one image would correspond to regions in another image which also consist of the similar grey values. Ideally, a ratio of the grey values for all corresponding points in a certain regions in both image may slightly vary. Consequently, an average variance of the ratio for all the regions may be minimized to achieve registration.

Mathematically, a representation of the mutual information based on Shannon entropy is as given below:

$$H(A) = \sum_i p_i \log_2(1/p_i)$$

$$H(A) = -\sum_i p_i \log_2 p_i$$

Consider, A and B to be two images. For the images A and B, the mutual information, represented as I may be defined as follows:

$$I(A,B)=H(A)+H(B)-H(A,B)$$

where,
H(A) and H(B) are Shannon entropies of A and B; and
H(A, B) is a joint entropy of A and B.
According to the Shannon entropy, H(A), H(B) and H(A, B) is represented as:

$$H(A) = -\sum_a p_A(a)\log_2 p_A(a)$$

$$H(B) = -\sum_b p_B(b)\log_2 p_B(b)$$

-continued $$H(A, B) = -\sum_{a,b} p_{AB}(a, b)\log_2 p_{AB}(a, b)$$

The mutual information may be modified for registering the one or more regions of interest. The one or more partial volumes in the one or more regions of interest may be selected from the result of the coarse registration. The modified mutual information (MMI) may be represented as $MI_0$. The MI may be modified to include a parameter related to an extent of an overlap (overlap rate) between the one or more regions of interest, represented as O. The extent of the overlap (overlap rate) may depend on a parameter defined by a user, represented as k. The parameter k may be a weight assigned to the overlap rate. If a value of k is 1 (one), then a result of the MMI may be very close to the result of the coarse registration. If the value of k is 0 (zero), then the result the MMI may be similar to original definition of the MI, and any geometrical transformation may be performed during the fine registration.

The modified mutual information may be represented as below:

$$MI_0(\vec{T})=MI(\vec{T})\cdot(1+k\cdot O)$$

where,
k is the weight defined by the user to the overlap varying between 0 and 1; and
O is the overlap rate varying between 0 and 1.

In one or more embodiments, the fine registration may be performed as mentioned below. A CT image and a MRI image may be selected. One or more regions of interest mat be identified. The CT image and the MRI image may be compared with a sample CT image and a sample MRI image. A rigid transformation may be applied to the CT image. The modified mutual information is computed for both the CT image and the MRI image. The modified mutual information may be computed repeatedly in order to maximize the MMI process through optimization to get a best result of the fine registration.

Figure 4:
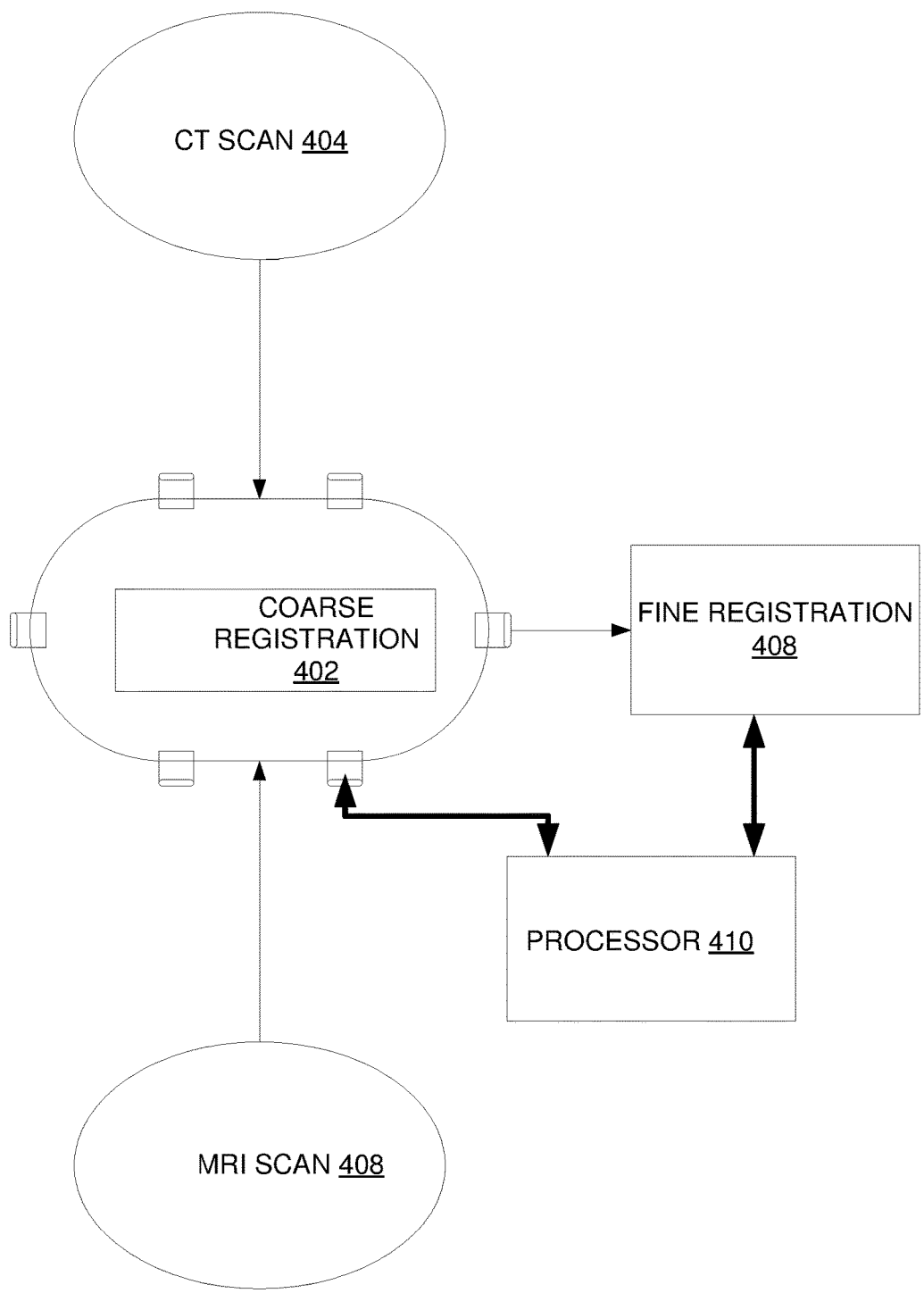
FIG. 4 is a multi-modal image registration system, according to one or more embodiments.

FIG. 4 is a multi-modal image registration system, according to one or more embodiments. In one or more embodiments, the multi-modal image registration system may include a processor 410, a coarse registration module 402 communicatively coupled to the processor, and a fine registration module 406 communicatively coupled to the coarse registration module. The coarse registration module 402, through the processor 410, may register multi-modal brain images such as CT scan 404 and MRI scan 408 through a projection based reference image. The coarse registration module, through the processor, may identify regions of clinical interest. The fine registration module may register the multi-modal brain images based on the identified regions of clinical interest using modified mutual information.

Figure 5:
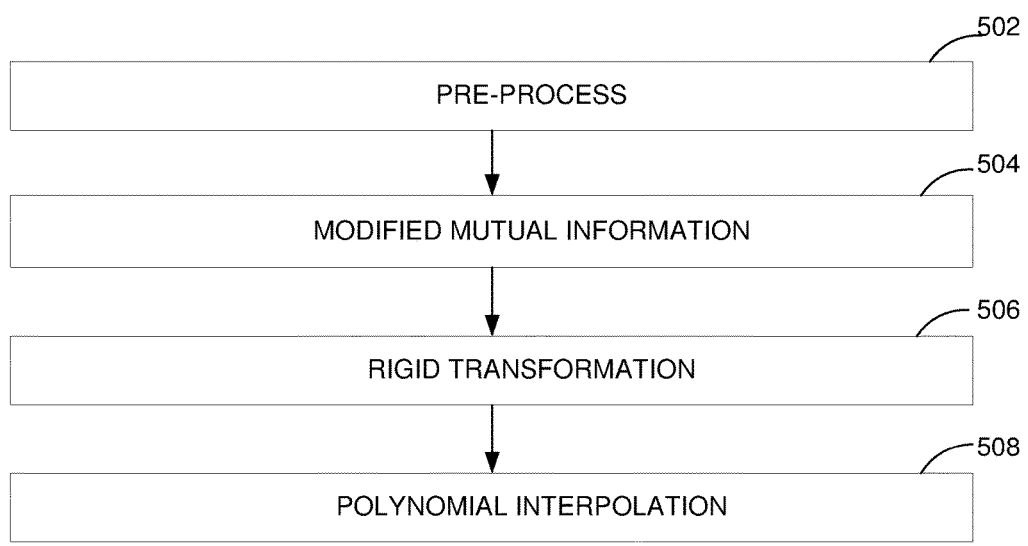
FIG. 5 is process flow diagram detailing the steps of registering multi-modal brain images, according to one or more embodiments.

FIG. 5 is process flow diagram detailing the steps of registering multi-modal brain images, according to one or more embodiments. In one or more embodiments, steps of registering multi-modal brain images may include pre-processing 502, calculating modified mutual information 504, rigid transformation 506, and polynomial interpolation 508.

In one or more embodiments, a method of image registration may include one or more of the following steps: pre-processing 502, mutual information 504, rigid transformation 506 and interpolation 508.

In one or more embodiments, pre-processing 502 may be necessary in order to improve input and reference image quality. Image enhancements may be performed by applying filters to remove any possible noise. Low-pass filtering and/or median filters may be applied to remove speckle noise in images. Images may also be normalized. Window-levelling may be performed as images from different modalities are getting registered. Both input and reference images may be resized to have equal width and height. In one or more embodiments, Shannon entropy may provide an absolute limit on a possible average length of lossless encoding and/or compression of communication. Shannon entropy measure may be used for computing a mutual information measure. The size of the overlapping part of the images may influence the mutual information measure in different ways. Hence, a normalized measure of mutual information (NMI) which is less sensitive to changes in overlap may be adopted and called modified mutual information (MMI) 504. The NMI may be used to identify registration points in a sample and/or reference image.

Post identification of the registration points, next step may be to define a transformation function to map the registration points. The transformation applied to register the images may be categorized according to the degrees of freedom. Rigid transformation 506 may include only translations and may be sufficient to register images of rigid objects. Other transformation techniques such as affine transforms may allow scaling and shearing.

Mutual information may be a registration measure for multimodality images. Mutual information may be based on the assumption that regions of similar tissue with similar grey values in one image would correspond to regions in the other image that also consist of similar grey values. Ideally, the ratio of the grey values for all corresponding points in a certain region in the one and the other images may vary a little. Consequently, the average variance of the ratio for all regions may be minimized to achieve registration.

Mathematically, a representation of the mutual information based on Shannon entropy is as given below:

$$H(A) = \sum_i p_i \log_2(1/p_i)$$

$$H(A) = -\sum_i p_i \log_2 p_i$$

Consider, A and B to be two images. For the images A and B, the mutual information, represented as I may be defined as follows:

$$I(A,B) = H(A) + H(B) - H(A,B)$$

where,
H(A) and H(B) are Shannon entropies of A and B; and
H(A, B) is a joint entropy of A and B.
According to the Shannon entropy, H(A), H(B) and H(A, B) is represented as:

$$H(A) = -\sum_a p_A(a) \log_2 p_A(a)$$

$$H(B) = -\sum_b p_B(b) \log_2 p_B(b)$$

$$H(A,B) = -\sum_{a,b} p_{AB}(a,b) \log_2 p_{AB}(a,b)$$

The mutual information (MI) is modified for registering the multi-modal brain images. The modified mutual information (MMI) may be represented as $MI_0$. The MI may be modified to include a parameter related to an extent of an overlap (overlap rate) between the one or more regions of interest, represented as O. The extent of the overlap (overlap rate) may depend on a parameter defined by a user, represented as k. The parameter k may be a weight assigned to the overlap rate. If a value of k is 1 (one), then a result of the MMI may be very close to the result of the registration of the multi-modal images. If the value of k is 0 (zero), then the result the MMI may be similar to original definition of the MI, and any geometrical transformation may be performed during the fine registration.

The modified mutual information may be represented as below:

$$MI_0(\vec{T}) = MI(\vec{T}) \cdot (1 + k \cdot O)$$

where,
k is the weight defined by the user to the overlap varying between 0 and 1; and
O is the overlap rate varying between 0 and 1.

Further, when transforming points from one image to another, interpolation may be required to estimate a grey value of the resulting point in a registration process. In addition, interpolation may be required to yield the registered image. Since interpolation may be performed only once, speed is less of an issue and a different choice of interpolation method may be more appropriate. In an example embodiment, linear interpolation may be the interpolation method adopted. Liner interpolation method may define an intensity of a point as the weighted combination of intensities of the point's neighbors. The weights may be linearly dependent on the distance between the point and the point's neighbors. Alternatively, polynomial interpolation 508 may also be used to estimate a grey value of the resulting point in the registration process.

In one or more embodiments, a method for a registration of multi-modal brain images is disclosed. The method includes receiving the multi-modal brain image. The multi-modal brain image may be but not limited to an image obtained through a computed tomography technique and/or a magnetic resonance imaging technique. A reference image may be considered for the registration. An input images may be, but not limited to a CT image and an MRI image. The input images i.e., the CT image and MRI image are processed.

The processing may be necessary in order to improve input and reference image quality. Image enhancements may be performed by applying filters to remove any possible noise. Low-pass filtering and/or median filters may be applied to remove speckle noise in images. Images may also be normalized. Window-levelling may be performed as images from different modalities are getting registered. Both the input images and the reference images may be resized to have equal width and height.

The resizing of the input images and the reference image may be performed based on sharing of mass technique. The input images and the reference image may be rotated and/or translated in the predetermined directions such as an axial, a sagittal and/or coronal directions. A convergence criteria may be applied to complete the resizing of the input images and the reference image.

Post the processing step, one or more registration points may be identified in both the CT image and the MRI image. Shannon entropy may provide an absolute limit on a possible average length of lossless encoding and/or compression of communication. Shannon entropy measure may be used for computing a mutual information measure. The size of the overlapping part of the images may influence the mutual information measure in different ways. Hence, a normalized measure of mutual information (NMI) which is less sensitive to changes in overlap may be adopted and called modified mutual information (MMI). The NMI may be used to identify the one or more registration points in the input images.

A transformation function may be defined through a modified mutual information (MMI). Based on the transformation function, the identified one or more registration points may be mapped with another registration points. The mapping steps may mean that registration points of one image is mapped with registration points of another image. By applying the transformation function, the input images may be registered. A rigid transformation may be used to register the input images. The rigid transformation may be sufficient to register images. In another embodiment, affine transformation may be used which allows scaling and shearing.

Further, when applying transformation function, interpolation may be required to estimate a grey value of the resulting point in a registration process. In addition, interpolation may be required to yield the registered image. In an example embodiment, linear interpolation may be the interpolation method adopted. Alternatively, polynomial interpolation may also be used to estimate a grey value of the resulting point in the registration process.

In one or more embodiments, a computer-implemented method for fusing one or more brain images based on a modified mutual information is disclosed. The method includes identifying one or more registration points in the two or more brain images. The one or more registration points may be registered based on a modified mutual information. Based on the modified mutual information a fused image of the two or more brain images may be generated.

Although the present embodiments have been described with reference to specific example embodiments, it will be evident that various modifications and changes may be made to these embodiments without departing from the broader spirit and scope of the various embodiments. For example, the various devices and modules described herein may be enabled and operated using hardware circuitry, firmware, software or any combination of hardware, firmware, and software (e.g., embodied in a machine readable medium). For example, the various electrical structure and methods may be embodied using transistors, logic gates, and electrical circuits (e.g., application specific integrated (ASIC) circuitry and/or in Digital Signal Processor (DSP) circuitry).

In addition, it will be appreciated that the various operations, processes, and methods disclosed herein may be embodied in a machine-readable medium and/or a machine accessible medium compatible with a data processing system (e.g., a computer devices), and may be performed in any order (e.g., including using means for achieving the various operations). The medium may be, for example, a memory, a transportable medium such as a CD, a DVD, a Blu-ray™ disc, a floppy disk, or a diskette. A computer program embodying the aspects of the exemplary embodiments may be loaded onto the retail portal. The computer program is not limited to specific embodiments discussed above, and may, for example, be implemented in an operating system, an application program, a foreground or background process, a driver, a network stack or any combination thereof. The computer program may be executed on a single computer processor or multiple computer processors.

Accordingly, the specification and drawings are to be regarded in an illustrative rather than a restrictive sense.

What is claimed is:

1. A computer-implemented method of registration of brain images comprising:
   registering, through a processor, at least two full volumes of brain images based on a projection based reference image, wherein the registration is performed based on a sharing of mass in a predetermined direction; and
   registering, through the processor, at least two partial volumes in regions of interest through modified mutual information, wherein the modified mutual information comprises mutual information modified to include a parameter related to an extent of overlap between the regions of interest and a weight assigned to the extent of overlap.

2. The method as claimed in claim 1, further comprising:
   defining, through the processor, a transformation function to map at least one registration point with another registration point.

3. The method as claimed in claim 1, wherein the registering based on the sharing of mass comprises:
   calculating, through the processor:
      rotation of the at least two full volumes of brain images in an axial, a sagittal, and a coronal direction; and
      translation of the at least two full volumes of brain images in an axial, a sagittal, and a coronal direction.

4. The method as claimed in claim 3, further comprising:
   applying, through the processor, at least one convergence criteria to complete the registration of the at least two full volumes of brain images.

5. The method as claimed in claim 1, wherein the mutual information comprises normalized mutual information.

6. The method as claimed in claim 1, wherein the registering based on the sharing of mass is further based on a distribution of mass determined via a brain atlas.

7. A multi-modal image registration system comprising:
   a processor;
   a coarse registration module communicatively coupled to the processor, wherein the coarse registration module, through the processor, registers multi-modal brain images through a projection based reference image, wherein the coarse registration module, through the processor, identifies regions of clinical interest; and
   a fine registration module communicatively coupled to the coarse registration module, wherein the fine registration module, through the processor, registers the multi-modal brain images based on the identified regions of clinical interest using modified mutual information, wherein the modified mutual information comprises mutual information modified to include a parameter related to an extent of overlap between the regions of clinical interest and a weight assigned to the extent of overlap.

8. The system of claim 7, wherein the course registration is performed based on sharing of mass in a predetermined direction.

9. The system of claim 8, wherein the coarse registration based on the sharing of mass comprises:
   calculating, through the processor:
      rotation of the multi-modal brain images in an axial, a sagittal, and a coronal direction; and
      translation of the multi-modal brain images in an axial, a sagittal, and a coronal direction.

10. The system of claim 9, further comprising:
    applying, through the processor, at least one convergence criteria to complete the registration of the multi-modal brain images.

11. The system of claim 7, wherein the mutual information comprises normalized mutual information.

12. A computer-implemented method of registration of multi-modal brain images comprising:
receiving, through a processor, at least two multi-modal brain images;
identifying, through the processor, at least one registration point in the at least two multi-modal brain images;
defining, through the processor, a transformation function through modified mutual information, wherein the modified mutual information comprises mutual information modified to include a parameter related to an extent of overlap between the at least two multi-modal brain images and a weight assigned to the extent of overlap;
applying, through the processor, the transformation function to map the at least one registration point with another registration point; and
interpolating, through the processor, to register the at least two multi-modal brain images.

13. The method of claim 12, further comprising, pre-processing, through the processor, the received at least two multi-modal brain images by applying at least one filter.

14. The method of claim 12, wherein the mutual information comprises normalized mutual information.

15. The method of claim 12, wherein the interpolation is performed through one of a polynomial interpolation technique and a linear interpolation technique.

16. A computer-implemented method for fusing at least two brain images based on modified mutual information, the method comprising:
identifying, through a processor, at least one registration point in the at least two brain images;
registering, through the processor, the at least one registration point based on modified mutual information, wherein the modified mutual information comprises mutual information modified to include a parameter related to an extent of overlap between the at least two brain images and a weight assigned to the extent of overlap; and
generating, through the processor, a fused image of the at least two brain images.

17. The method of claim 16, further comprising:
defining, through the processor, the transformation function to map the at least one registration point with another registration point.

18. The method of claim 16, wherein the at least one registration point contains at least one deep brain structure.

19. The method of claim 16, wherein the mutual information comprises normalized mutual information.

20. The method of claim 16, wherein at least one image of the at least two brain images is an image obtained through one of a computed tomography technique and a magnetic resonance imaging technique.

* * * * *